United States Patent [19]

Russell et al.

[11] Patent Number: 5,556,710

[45] Date of Patent: Sep. 17, 1996

[54] METAL COATING USEFUL FOR RENDERING THE SURFACE OF THE METAL BIOCOMPATIBLE

[75] Inventors: Jeremy C. Russell; Yiannakis P. Yianni, both of Middlesex; Stephen A. Charles, Oxon, all of United Kingdom

[73] Assignee: Biocompatibles Limited, Middlesex, United Kingdom

[21] Appl. No.: 331,529

[22] PCT Filed: Apr. 23, 1993

[86] PCT No.: PCT/GB93/00853

§ 371 Date: May 3, 1995

§ 102(e) Date: May 3, 1995

[87] PCT Pub. No.: WO93/22320

PCT Pub. Date: Nov. 11, 1993

[30] Foreign Application Priority Data

Apr. 24, 1992 [GB] United Kingdom .................. 9208950
Nov. 16, 1992 [GB] United Kingdom .................. 9224031

[51] Int. Cl.$^6$ .............................. B32B 15/04; C07F 9/09
[52] U.S. Cl. .............................. 428/457; 546/24; 558/166; 558/169; 558/170
[58] Field of Search ................... 546/24; 558/166, 558/169, 170; 428/457

[56] References Cited

U.S. PATENT DOCUMENTS 4,492,659  1/1985  Bosies et al. ............................ 558/169
5,380,904  1/1995  Chapman et al. ....................... 558/166

Primary Examiner—Johann Richter
Assistant Examiner—Michael G. Ambrose
Attorney, Agent, or Firm—Sughrue, Mion, Zinn, Macpeak & Seas

[57] ABSTRACT

Compounds of formula (I), in which the groups R are hydrogen or $C_{1-4}$ alkyl, n is from 2 to 4, X is alkylene, poly(ethoxy) or an aryl-containing group, Y is a valence bond or a divalent functional or heterocyclic group or a trivalent alkylene group, and Z is a sulphur-containing group which contains a thiol or disulphide group are useful to provide biocompatible treatments of metal surfaces, such as silver and gold surfaces. Processes for the preparation of the compounds, intermediates useful in such processes, articles having a metal surface treated with such compounds and processes of rendering metal surfaces biocompatible which comprise treating the metal surfaces with them.

12 Claims, No Drawings

METAL COATING USEFUL FOR RENDERING THE SURFACE OF THE METAL BIOCOMPATIBLE

This application was filed under 35 U.S.C. 371 and was upon PCT International Application No. PCT/GB93/00853, filed Apr. 23, 1993.

This invention relates to new compounds useful as metal coatings to render metal surfaces biocompatible, a process for their preparation, and their use in rendering a metal surface biocompatible.

The clinical use of blood contacting devices and prostheses is of major importance today in cardiovascular surgery and other fields of medicine. Heart valves and blood vessel prostheses, balloon pumps and catheters are being implanted in daily surgical practice to restore or diagnose cardiovascular function. Artificial organs are routinely employed in blood detoxification by absorptive haemoperfusion and in oxygenation (membrane oxygenators and heart-lung devices). Considerable effort and capital is invested in Europe and the U.S.A. in the development and experimental evolution of an implantable artificial heart system. The devices are commonly constructed from metals and, when in use, a blood-metal contact is present. This contact will cause a reaction in the recirculating blood, which, depending on the choice of metal, the design parameters, the flow or the addition of the anticoagulants, may lead to protein deposition, adhesion and destruction of red blood cells (haemolysis), platelet (thrombocyte) adhesion and aggregation and blood coagulation leading to formation of a haemostatic plug (thrombus). The occurrence of thromboembolism in cardiovascular surgery continues to be a problem, notwithstanding routine treatment with anticoagulants. For these reasons the search for biocompatible non-thrombogenic materials has been an important research objective over the last two decades.

In addition, certain diagnostic procedures designed for the rapid analysis of analytes in body fluids are compromised by non-specific binding of fluid components. This problem is particularly acute in biosensors which use parameters such as the mass or the refractive index of the analyte to determine analyte concentration. For instance, small changes in refractive index associated with the binding of body fluid components to a metal film can be measured using surface plasmon resonance (SPR).

We have now devised new compounds which aim to mimic some of the interfacial characteristics of the outer cell surface of for example red blood cells, and in particular the lipid component of the biological membrane which is the simplest common factor of such surfaces. The compounds are derivatives or analogues of phosphorylcholine that can be linked to the metal surface which is to be rendered biocompatible via a thiol or disulphide functional group in the compounds. This deposits a phosphorylcholine type of residue on a surface. Such residues are commonly found in lipid membranes.

Accordingly the present invention provides compounds of formula (I)

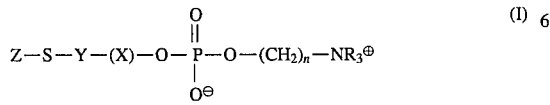

in which the groups R are the same or different and each is hydrogen or a straight or branched $C_1$–$C_4$ alkyl group, preferably methyl; n is from 2 to 4, preferably 2, and X is a straight or branched $C_{1-30}$ alkylene group, preferably a group of formula —$(CH_2)_a$—, or X is a group of formula —$(CH_2CH_2O)_b$—, or —$(CH_2)_c$—Ar—$(CH_2)_d$— where a is from 1 to 30, b is from 1 to 20, c and d are the same or different and each is from 0 to 5, and Ar is a para- or meta-disubstituted aryl group such as a phenyl, biphenyl or naphthyl group (preferably a para-disubstituted biphenyl group) which is optionally further substituted by one or more $C_1$–$C_4$ alkyl groups; and either Y is a valence bond or a divalent functional or heterocyclic group; and Z is hydrogen or a group —$SZ^1$ where $Z^1$ is an alkyl, cycloalkyl, alkylcycloalkyl, aryl, alkylaryl, heterocyclic, alkylheterocyclic group or a group of formula (II):

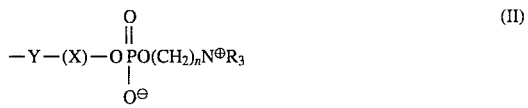

where Y, X, R and n are as hereinbefore defined; or

Y is a trivalent alkylene group,

Z is a group —$SZ^1$ and $Z^1$ is an alkylene group, unsubstituted or substituted by alkyl, aryl, alkylaryl, cycloalkyl or alkylcycloalkyl groups and bonded to the group Y so —Y—S—$Z^1$ form a 5 to 8 membered, preferably 5 or 6 membered, ring containing a disulphide linkage;

or a hydrate thereof.

Without wishing to be limited by the theory of the invention, it is thought that when metal surfaces are treated with the compounds of the present invention, the thiol or disulphide bond, is cleaved and a new bond is formed between the metal surface and the sulphur atom.

Particularly preferred compounds of formula (I) are those in which X is —$(CH_2)_a$— and a is from 1 to 30, preferably 1 to 20, more preferably 12 to 18. In an alternative embodiment x is a group —$(CH_2)_a$— where a is from 1 to 8, more preferably 2 to 6. Other preferred compounds are those wherein X is —$(CH_2CH_2O)_b$— and b is from 1 to 7: those compounds in which X is —$(CH_2CH_2O)_b$—, particularly when b is higher than 7 (e.g. 8 to 10), tend to exist as mixtures of compounds with different values of b rather than as pure single compounds. The value of b may, therefore be fractional, representing an average value for the mixture of these compounds. The compounds in which X is —$CH_2$(p—$C_6H_4$) $CH_2$—, —$CH_2$(p—$C_6H_4$)—, —(p—$C_6H_4$)$CH_2$—, —(p—$C_6H_4$)—, —$CH_2$(p—$C_6H_4C_6H_4$)$CH_2$—, —$CH_2$(p—$C_6H_4C_6H_4$)—, —(p—$C_6H_4C_6H_4$)$CH_2$— or —(p—$C_6H_4C_6H_4$)— are preferred.

Compounds of formula (I) in which R is hydrogen, methyl, ethyl, n-propyl or n-butyl are also preferred, as are compounds in which all the R groups are the same.

Particularly preferred are the compounds of formula (I) which contain a phosphorylcholine moiety, ie in which each R is methyl and n is 2.

One particularly preferred combination is when the compound of formula (I), contains a phosphorylcholine moiety and X is a group of formula —$(CH_2)_{12}$— or —$(CH_2)_6$—, i.e. dodecoxy- or hexoxyphosphinyloxy-N,N,N,-trimethylethanaminium hydroxide inner salts.

As the divalent functional or heterocyclic group, Y, mention may be made in particular of the following combination of S-Y:

—S($X^1$)C(=T)N(H)—, where $X^1$ is as defined above, preferably a straight or branched chain alkylene group, containing from 1 to 20 carbon atoms, such as $(CH_2)_{1-20}$, preferably $(CH_2)_{1-6}$, e.g. $(CH_2)_2$, and T is oxygen or sulphur, preferably oxygen;

—SC(=T)— where T is oxygen, sulphur or NH, preferably oxygen or sulphur;

—SC(=T)N(H)— where T is oxygen, sulphur or NH, preferably oxygen or sulphur; or

—SHet-Y$^1$— where Y$^1$ is a single bond, oxygen or sulphur, or an alkoxy or alkylthio group containing from 1 to 10 carbon atoms, and Het is a heterocyclic group, e.g. a pyridyl, pyrazinyl, pyriminidyl, triazinyl, quinolyl, isoquinolyl, pyrrolyl, furyl, thienyl, thiazolyl, isothiazolyl, diazathiazolyl, e.g. 1,3,4 thiadiazolyl, piperidyl, piperazyl and sugar rings, e.g. glucose. Particular mention may be made of the following linking groups containing heterocyclic rings:

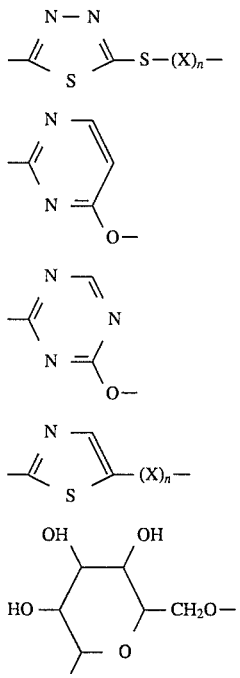

If the group Z$^1$ is an alkyl group it may be straight or branched and contain typically from 1 to 10 carbon atoms.

If Z$^1$ is a cycloalkyl or alkyl cycloalkyl group then typically the cycloalkyl ring contains from 5 to 8 carbon atoms and is unsubstituted or substituted by one or more alkyl groups, typically containing from 1 to 4 carbon atoms. In the case of an alkylcycloalkyl group the alkyl portion typically contains 1 to 10 e.g. 1 to 6 carbon atoms and is straight or branched.

If Z$^1$ is an aryl or alkylaryl group, then typically the aryl is a phenyl or naphthyl ring which is unsubstituted or substituted by one or more alkyl groups, typically containing from 1 to 4 carbon atoms. In the case of an alkylarylalkyl group the alkyl portion typically contains 1 to 10 e.g. 1 to 6 carbon atoms and is straight or branched.

If Z$^1$ is a heterocyclic or alkyl heterocyclic group the typically the heterocycle is a pyridyl, pyrazinyl, pyriminidyl, triazinyl, quinolyl, isoquinolyl, pyrrolyl, furyl, thienyl, thiazolyl, diazathiazolyl, e.g. 1,3,4-diazathiazolyl, piperidinyl or piperazyl group, which is unsubstituted or substituted by one or more alkyl groups containing typically from one to four carbon atoms. A particularly preferred embodiment is when Z$^1$ is a 2-pyridyl group.

If the group Z$^1$ is a group of formula (II) then it is preferred that the compound of formula (I) is a symmetrical disulphide.

Where the group Z$^1$ is an alkylene group bonded to the trivalent alkylene group Y to form a ring containing a disulphide linkage; then preferably Z$^1$—S—S—Y— is a group of formula

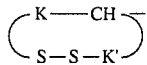

wherein K and K' are the same or different and each is a valence bond or an alkylene group of 1 to 5 carbon atoms, unsubstituted or substituted by alkyl, aryl, alkylaryl, cycloalkyl or alkylcycloalkyl groups, provided that the ring containing K and K' is a 5 to 8 membered ring, preferably 5 to 6 membered, ring.

Preferably, where K or K' is an alkylene group it is unsubstituted, or if substituted, the substituents are alkyl, aryl, alkylaryl, cycloalkyl or alkylcycloalkyl groups as described above in relation to Z$^1$. It is preferred that K be a group —(CH$_2$)$_{2-5}$—, e.g. —(CH$_2$)$_2$—, and K' valence bond.

According to a further feature of the present invention, there is provided a process for preparing the compounds of formula (I) which comprises:

(a) reacting a compound of formula (III)

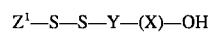

in which X and Z$^1$ are as hereinbefore defined and Y, with a compound of the formula (IV)

in which n is as hereinbefore defined and Hal is a halogen, preferably chlorine, to provide a compound of formula (V)

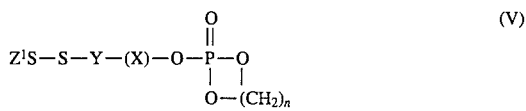

in which Z$^1$, X and n are as hereinbefore defined, reacting the compound of formula (V) with NR$_3$, where R is as hereinbefore defined to provide a compound of formula (I) wherein Z is a group Z$^1$S, and Y is a valence bond or a trivalent alkylene group bonded to Z$^1$ to form a ring containing a disulphide linkage;

(b) converting a compound of formula (VI)

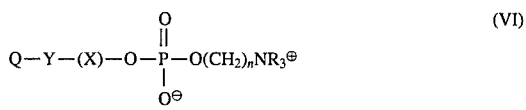

where Q is a halogen, preferably chlorine, bromine or iodine, e.g. bromine, or Q is a readily displaceable leaving group, such as tosyl or mesyl, or Q is a protected thiol group, e.g. a thioether or thioester, Y is a valence bond or a divalent heterocyclic group and X and R and n are as hereinbefore defined, to a compound of formula (I) in which Z is hydrogen, and if desired converting the compound thus obtained to a disulphide of formula (I) in which Z$^1$ is a group of formula (II);

(c) reacting a compound of formula (VII)

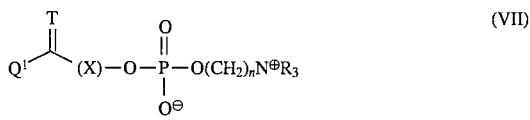

where $Q^1$ is halogen, e.g. chlorine or bromine or a readily displaceable leaving group, such as tosyl or mesyl, T is oxygen or sulphur, and X, R and n are as hereinbefore defined with a sulphur-containing compound e.g. sodium sulphydride, to form a compound of formula (I) where Y is a group of formula, >C=O or >C=S and Z is H (d) reacting a compound of formula (VII) where T is sulphur with an alcohol and then ammonia to provide a compound of formula (I), where Y is a group of formula >C=NH and Z is H;

(e) reacting a compound of formula (VIII):

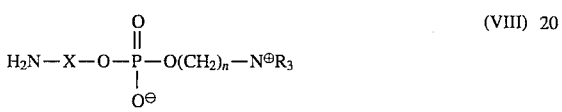

where X, R and n are as defined hereinbefore with a compound of formula (IX).

where $Z^1$ and X are as hereinbefore defined, T is oxygen or sulphur and $Q^3$ is a readily displaceable group, such as halogen, oxyamino, e.g. N-succinimidyl or a group of formula

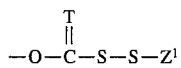

($Z^1$ and T being the same as in formula (IX)), to form a compound of formula (I) in which Z is S, and Y is —C(=T)NH—;

(f) reacting a compound of formula (X)

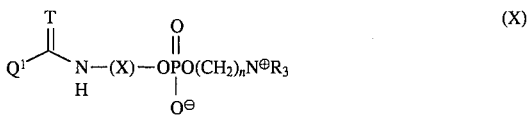

where T is oxygen or sulphur and $Q^1$, X, R and n are as hereinbefore defined with a sulphur containing compound e.g. sodium sulphydride to fork a compound of formula (I) where Y is a group of formula —C(=T)NH— and Z is H;

(g) reacting a compound of formula (X) as hereinbefore defined where T is sulphur with an alcohol and then $NH_3$ to provide a compound of formula (I) where Y is a group of formula —C(=NH)NH— and Z is H;

(h) converting a compound of formula (I) where Z is hydrogen to a compound of formula (I) where Z is a group $SZ^1$, as hereinbefore defined; or (i) converting a compound of formula (I) where Z is a group $SZ^1$, as hereinbefore defined to a compound of formula (I) where Z is hydrogen; and if desired, converting the resulting product to a hydrate thereof.

The invention also provides, as a further feature, the new compounds of formula (VI), (VII) and (X) as hereinbefore defined, which are useful as intermediates in the preparation of compounds of formula (I).

For the preparation of a compound of formula (I) by route (a), the alcohol (III) is typically dissolved in an organic aprotic solvent (typically acetonitrile, N,N'-dimethylformamide, or dichloromethane for example acetonitrile) and then treated with one equivalent of a compound of formula (IV), e.g. 2-chloro-2-oxo-1,3,2-dioxaphospholane, in the presence of a base (typically sodium or potassium carbonate, triethylamine or N,N,dimethylaminopyridine for example anhydrous sodium carbonate). This gives a cyclic phospholane of formula (V) as an intermediate which is typically treated with appropriate nitrogenous base (for example trimethylamine) under anhydrous conditions in a pressure bottle with an aprotic solvent (for example acetonitrile). This reaction is generally performed for 3 to 73 hours, (typically 18–24 hours, for example 18 hours) at a temperature of 0 to 100° C., (typically 60° to 75° C. for example 70° C.). The resulting compound of formula (I) may be isolated by column chromatography, using for example silica gel, or by for example crystallisation.

The compounds of formula (III) in which Y is a valence bond may be obtained by reacting a hydroxythiol compound of formula (XI)

where X is as hereinbefore defined with a disulphide $(Z^1S)_2$, generally in an organic solvent (for example ethanol and acetic acid mixtures) and isolated by silica gel chromatography. Typically the reaction is performed at 0°–40° C. for example for 18 hours. The hydroxythiols of formula (XI) may be obtained commercially or by known method.

The compounds of formula (III) in which Y is bonded to $Z^1$ to form a ring containing a disulphide linkage may be obtained by intra-molecular oxidation of the corresponding dithiol to form a disulphide using for example hydrogen peroxide, see for example Vogel, Practical Organic Chemistry, by B. S. Furniss, A. J. Hannaford, P. W. G. Smith and A. R. Tatcheil, Published by Longman, 1989. The corresponding dithiol compounds may be obtained from dibromo compounds by reaction with a sulphur containing compound, e.g, sodium sulphydride, thiourea or sodium thiosulphate, or these compounds may be commercially available. The dibromo compounds may be obtained commercially or using known techniques.

Where it is desired to prepare a compound of formula (I) by method (b), when Q is halogen or a readily displaceable group such as tosyl or mesyl then an appropriate compound of formula (VI) may be converted to a compound of formula (I), where Z is hydrogen by reaction with various reagents (typically thiosulphate, e.g. sodium or potassium thiosulphate, then hydrochloric acid, sulphydride e.g. sodium sulphydride or thiourea and sodium or potassium hydroxide). The product thus obtained may be purified, for instance by chromatography (typically silica gel, or alumina) and/or isolated for instance by crystallisation (in for example methanol and acetone). Where it is desired to prepare a compound of formula (I) by method (b), when Q is a protected thiol group then suitable protecting groups include thioethers, e.g. tritylthioether, tert-butylthioether, 2–4-dinitrophenylthioether and benzylthioether, thioesters and silylthioethers e.g. diphenylmethylsilylether. These groups may be added and removed using known techniques as described for example in Vogel, supra, and Advanced Organic Chemistry, J. March, published J. Wiley, 3rd edition 1985.

If for example a thioether such as tritylthioether is used then a range of conditions (typically trifluoroacetic acid, in methanolic hydrogen chloride, hydrobomic acid in acetic acid or for example silver nitrate in methanol) at temperatures of 0° to 100° C. (for example 30° C.) may be used to convert an appropriate compound of formula (IV) to a compound of formula I in which Z is hydrogen. The product may be purified by chromatography (for example silica gel) or by crystallisation (for example from methanol or acetone).

The compounds of formula (VI) may be obtained by a procedure analogous to that described under (a), but starting from compounds of formula (XII)

Q—(X)—OH    (XII)

The compounds of formula (XII) may be obtained commercially or by using known methods. In the case where Q is —SCPh$_3$, they may in particular be prepared by the reaction of mercaptotriphenylmethane with an inorganic base (for example potassium carbonate) followed by reaction with a compound of formula (XII) in which Q is halogen, e.g. bromine, or tosyl or mesyl in an aqueous solvent mixture (for example water and ethanol).

The compound for formula (I) in which Z is hydrogen, thus produced, may be converted to a disulphide in which. Z is Z$^1$S and Z$^1$ is a group of formula (II) using known methods for the formation of disulphides form thiols, using for example hydrogen peroxide as described in Vogel, supra.

If it is desired to obtain a compound of formula (I) by route (c) or (d) the appropriate compound of formula (VI) may be first converted to a metallo reagent e.g. a Grignard reagent by reaction with magnesium by known methods. The metallo-derivative may then be reacted with a compound Q$^1{}_2$C=T where each Q$^1$ is the same or different and is as defined above, typically in the presence of a base e.g. triethylamine and Li$_2$CuCl$_4$.

According to (c) a compound of formula (VII) which may be obtained thus may be treated with a sulphur containing compound, e.g. sulphydride, thiosulphate or thiourea, e.g. sodium sulphydride to obtain a compound of formula (I) where Y is >C=O or >C=S.

According to (d) a compound of formula (VII) in which T is sulphur may be treated with an alcohol, e.g. ethanol, followed by ammonia to obtain a compound of formula (I) where Y is >C=NH.

If it is desired to prepare a compound of formula (I) by route (e) an appropriate compound of formula (VIII) is reacted with an appropriate compound of formula (IX). Typically the compound of formula (VIII) is taken up in a solvent, typically an aqueous buffer or a polar aprotic organic solvent (for example dimethyl sulphoxide). The compound of formula (IX) is then added in an organic solvent, typically ethanol or a mixture of dimethylsulphoxide and triethylamine. The mixture is generally stirred at 0° to 40° C. (for example 27° C.) for one to 24 hours (for example 18 hours) and the product typically purified by column chromatography.

The compounds of formula (IX) may be prepared by known methods. For example compounds of formula (IX) may be obtained by reaction of a thiol HS—X—C(=T)Q$^3$ with a disulphide (Z$_1$S)$_2$. This reaction may be performed using the conditions described for the formation of the disulphides of formulae (III) described above. The thiols HS—X—C(=T)Q$^3$ may be prepared using known techniques.

The compounds of formula (VIII) may be prepared by a procedure analogous to that described above in relation to (a), but starting from a protected amino alcohol of formula (XII):

R'R''N—(X)—OH    (XIII)

The coupling of the N-protected alcohols of formula (XIII) to the compounds of formula (IV) may be performed in the presence of a base under anhydrous conditions. The reaction is typically performed at a temperature from −5° to 50° C. (preferably 10° to 30° C., e.g. 25° C.) in a dry organic solvent, e.g. acetonitrile or N,N-dimethylformamide and in the presence of an organic base, such as a tertiary amine, e.g. triethylamine or pyridine, or an inorganic base, such as an alkali metal carbonate, e.g. sodium carbonate.

The ring opening reaction may, for example, be performed in tertiary amine, e.g. trimethylamine, at a temperature from 20° to 100° C., preferably 40° to 80° C., e.g. 70° C., and in a sealed pressure vessel for 3 to 72 hours (e.g. 18 hours).

The deprotection may be performed as a separate step after or, in some cases, before the ring-opening reaction. It may also be performed at the same time as the ring-opening reaction.

The protecting groups are chosen so that they do not react with the compounds of formula (IV). As examples of particular protecting groups there may be mentioned:

amides (NR' and/or NR" is an amide group), e.g. N-phthalimides;

carbamates (NR' and/or NR" is a carbamate group), e.g. 9-fluorenylmethoxycarbonylamines, or teftbutyloxycarbonylamines;

hindered secondary amines, (R' is a hindered group e.g. triphenylmethyl and R" is H); or salts, (NR'R" is a NH$_3{}^+$A$^-$group). Suitable counter ions A$^-$ are anions of organic acids, such as acetic or p-toluene sulphonic acid or inorganic acids such as hydrogen halides, e.g. hydrogen chloride.

The N-protected aminoalcohols of formula (XIII), may be prepared from bromoalcohols of formula (XIV) or aminoalcohols of formula (XV) which are commercially available or may be prepared by known methods:

Br—(X)—OH    (XIV)

H$_2$N—(X)—OH    (XV)

In some cases however, the protected amine alcohols are themselves commercially available e.g. N-(2hydroxyethyl)phthalimide.

In the case where the protecting group is an amide the protected amino alcohol may be prepared from either the bromoalcohol of formula (XIV) or the aminoalcohol of formula (XV) by known methods. For example if the protecting group is a phthalimide, the protected amino alcohol is obtained by reaction with an alkali metal phthalimide, e.g. potassium phthalimide. Typically the reaction with phthalimide is performed in an organic solvent such as N,N-dimethylformamide at a temperature from 70° to 110° C. e.g. 90° C. After coupling to a phosphorus compound of formula (IV) and ping-opening, deprotection is performed under basic conditions (for example, in aqueous hydrazine). This gives the final product of formula (VIII) which can be purified for instance by column chromatography using, for example, silica gel.

In the case where the protecting group is a carbamate, protection is afforded by reaction of an amino alcohol with, for example, a chloroformate or acid anhydride to give a carbamate. The reaction is generally performed in an organic solvent, at a temperature from 10 to 50° C. and in the presence of a base. 9-Fluorenylmethoxychloroformate, for example, reacts with amines to give 9-fluorenylmethoxycarbonylamine derivatives and di-tert-butyldicarbonate reacts with amines to give tert-butyloxycarbonylamine derivatives. Ethanolamine, for example, reacts with 9-fluorenylmethoxychloroformate under anhydrous conditions in an inert solvent such as dichloromethane, in the presence of a suitable base such as pyridine, in a temperature range of, for example, –10° C. to 50° C., for example, 10° C., to give N-9-fluorenylmethoxycarbonylaminoethanol. Ethanolamine reacts with di-tert-butyldicarbonate under aqueous conditions, for example, aqueous 1,4-dioxan, in the presence of a suitable base, for example sodium hydroxide, at a suitable temperature, for example –10° C. to 50° C., preferably at 0° C., to give N-tert-butyloxycarbonyl-aminoethanol.

The carbamate protecting groups may be removed after the coupling reaction by known methods. For example the N-9-fluorenylmethoxycarbonyl amine protecting group may be removed under basic conditions in a suitable solvent, such as acetonitrile. Suitable bases for amine deprotection include ammonia, dialkylamines such as diethylamine, trialkylamines such as trimethylamine, cyclic amines and especially cyclic secondary amines such as morpholine, piperazine, piperidine and diazabicyclic bases such as 1,5-diazabicyclo(4.3.0)non-5-ene (DBN) and 1,8-diazabicyclo(5.4.0)undec-7-ene (DBU). The deprotection conditions may be chosen such that deprotection is performed prior to ring-opening or at the same time. The tert-butyloxycarbonyl amine protecting group may be removed using a suitable acid, for example trifluoroacetic acid or hydrochloric acid. The reaction may be performed in a suitable solvent system, for example, 1,4-dioxan/chloroform mixtures at a temperature of 0° to 50° C., for example, 21° C.

In the case where the protecting group is a hindered secondary amine the protected aminoalcohol (VIII) may be prepared by initial blocking of the hydroxyl function (for example, by reacting with chlorotrimethylsilane) in an organic solvent (for example, tetrahydrofuran) in the presence of an organic base (for example triethylamine). The amine function is then protected using a hindered chloroalkane (for example, chlorotriphenylmethane) in the presence of an organic base (for example, triethylamine). The hydroxyl function is then deprotected under mild conditions (for example, with methanol).

After coupling and ring opening, deprotection may be performed under acidic conditions, for example, with trifluoroacetic acid or with hydrogen chloride gas, in a non-aqueous solvent, for example, 1,4-dioxan, or chloroform. This gives the crude product which can be purified by column chromatography using, for example, silica gel.

If NR'R" is $NH_3^{\oplus}A^{\ominus}$ in the protected aminoalcohol of formula (VIII), it will react with the compound of formula (VIII) selectively via the hydroxyl group. Protected aminoalcohols in which NR'R" is $NH_3^{\oplus}A^{\ominus}$ are prepared by protonation with a suitable acid. Suitable acids include inorganic and organic acids especially p-toluenesulphonic acid which gives with, for example, ethanolamine, a crystalline p-toluenesulphonate which is soluble in a solvent suitable for the reaction with (III), for example, acetonitrile.

After coupling, these amine salts may be converted to free amines under suitable basic conditions using, for example, trimethylamine. Advantageously, the protected amine salts are ring-opened and converted to free amines in a single step using trimethylamine. In the case where the acid addition salt is desired it is not necessary to deprotect the amine group.

If it is desired to obtain a compound of formula (I) using method (f) or (g), the appropriate compound of formula (VIII) may be first reacted with a compound, $Q^1_2C=T$ typically in the presence of a base to provide the appropriate compound of formula (X). According to (f) the compound of formula (X) may then be reacted with a sulphur-containing compound, e.g, a sulphydride, thiosulphate or thiourea, e.g. sodium sulphydride to obtain a compound of formula (I) in which Y is —C(O)NH— or —C(S)NH—. According to (g) the compound of formula (X) may be treated with an alcohol, e.g. ethanol, followed by ammonia to obtain a compound of formula (I) in which Y is —C(=NH)NH—.

If it is desired to obtain a compound of formula (I) by route (h), then an appropriate compound of formula (I) where Z is hydrogen, may be reacted with a disulphide of formula $(Z^1S)_2$. Generally the reaction is performed in an organic solvent (e.g. ethanol and acetic acid mixture). Typically the reaction is performed at 0°–40° C. for example for 18 hours.

The compounds of formula (I) in which Z is $Z^1S$ may be converted to compounds of formula (I) in which Z is hydrogen according to method (i) using known methods for the formation of disulphides. For example the reaction may be performed using zinc in dilute acid, e.g. HCl or using triphenylphosphine in water as described in March and Vogel, supra.

Hydrates of the compounds of formula (I) may be produced by the above methods or they may be formed by an additional separate step, using known methods.

As a further feature, the present invention provides a process for rendering a metal surface biocompatible, which process comprises applying to the surface a compound of formula (I) or a hydrate thereof.

Metals which may be derivatised in this way include aluminium, tin, titanium, iron, silver, gold, platinum, chromium, copper, nickel, palladium, tungsten and alloys containing these. In particular the compounds of formula (I) may be used to treat silver and gold.

Treatment may typically be affected with a solution of the compound of formula (I) or hydrate thereof in for example aqueous buffer, e.g. phosphate buffer, methanol or ethanol. The treatment is typically carried out at a temperature from –20° to 100°, preferably 0° to 50° C., e.g. about 27° C., and for period of typically up to 96 hours. Treatment may be carried out for example, in methanol, ethanol or aqueous buffer, e.g. phosphate buffer. If aqueous buffer is used the pH is typically from 4 to 9, such as 5 to 8, preferably about 7.5.

Pre-treatment of the metal surface, for example by heating, electrolysis or chemical activation may be required in order to enhance the reactivity of some metal surfaces towards the compounds of formula (I).

Silver may for example be readily treated with a compound of formula (I) or a hydrate thereof at 0° to 50° C., e.g. ambient temperature, in an organic solvent, for example methanol, or in phosphate buffer, typically at a pH from 4 to 9, preferably 5 to 8, e.g. 7.5, for 24 hours. Gold may be treated at typically 0° to 50° C., e.g. ambient temperatures with a solution of compound formula (I) or a hydrate thereof 1 to 96 hours. Other metals, such as titanium, platinum, chromium and copper may be heated (for example at 50° to 250° C.) prior to exposure to a compound of formula (I), which is for example a thiol, or a hydrate thereof. Other metals e.g. palladium and platinum may be reacted with a compound of formula (I) or hydrate thereof under electrolytic conditions. Metals such as aluminium may require chemical activation before derivatisation see for example Advanced Inorganic Chemistry, by F. A. Cotton and G. Wilkinson 3rd Edition 1972, published by Interscience.

As a further feature the invention also provides an article having a metal surface to be introduced into the human or animal body or which is to be brought into contact with body cells or fluids or into contact with protein solutions which surface has been treated with a compound of formula (I) or a hydrate thereof.

Articles having metal surfaces to which compounds of formula (I) have been attached show reduced protein adsorption at that surface and increased haemocompatibility.

The present invention will now be further illustrated by means of the following Examples:

EXAMPLES

The following assays have been used to evaluate coatings on surfaces of compounds according to the present invention.

Protein adsorption using an enzyme immunoassay

The assay determines absorption of human fibrinogen at a surface. This protein is representative of protein which is typically adsorbed at a surface. The assay can be readily modified to determine the absorption of other proteins.

Discs (5 mm in diameter) of metal (as controls) and metal treated with compound as described below, were prepared and washed with phosphate buffered saline (PBS) for at least 10 minutes in the wells of microplates. The samples were incubated with human plasma (300 µl) for 10 minutes and then washed with PBS three times. Each of the test samples and each of the control samples were treated with human fibrinogen-specific antibody (300 µl) for 30 minutes and again washed with PBS three times. As a control for non-specific binding of antibody to the samples, each sample was also incubated with non-specific antibody (300 µl) for 30 minutes. A conjugate of horseradish peroxidase and a second antibody specific to the first antibody (300 µl) was added to both the test samples and the controls and incubated for 30 minutes before washing. Each of the test samples and the controls were transferred to new microplates and a solution of 2,2'-azino-bis(3-ethyl benzthiazoline-6-sulphonic acid) (ABTS) in phosphate-citrate buffer (300 µl, 0.6 mg/ml) added, the reaction was allowed to proceed for 10 minutes. At this time an aliquot of the mixture (200 µl) was removed and added to a solution of citric acid and sodium azide in distilled water (20 µl, 0.21 g/ml and 2 mg/ml respectively). The optical density of the solutions was measured using a Techgen automated plate reader at 650 nm using the ABTS solution as blank.

In an alternative procedure, rather than using ABTS, each of the samples was transferred to wells of new microplates and a solution of o-phenylene diamine (OPD) in phosphate-citrate buffer (300 µl, 0.4 mg/ml) added, and the reaction was allowed to proceed for 10 minutes. At this time an aliquot of the mixture (200 µl) was removed from each well and the optical density of the solutions was measured using a Techgen automated plate reader at 450 nm using the OPD solution as blank.

Activated Platelet Study

Blood was collected from a healthy adult volunteer using the double syringe method where the first 5 ml of blood is discarded. The blood was collected into tri-Sodium citrate (32 g/l) in the proportion of 9 volumes to 1 volume citrate in plastic tubes. The samples were kept at room temperature on a spiral mixer until used.

Discs (5 mm in diameter) of metal as controls and material treated with compounds as described below were prepared and placed into the wells of a microplate. Half of the test replicates were incubated with citrated blood (200 µl) and the remainder were incubated with EDTA-treated blood on a phase shaker for 30 minutes before washing in PBS four times. Platelet activation was measured by a propriety assay (EJ Campbell et al, Mat. Res. Soc. Symp. Proc. 252, 229–237). The procedure is analogous to that described above for detection of proteins by enzyme immunoassay but uses antibodies against GMP140 to detect the presence of this platelet activation marker on the surface of biomaterials. In the presence of EDTA, which extracts calcium from inside platelets, activation is inhibited, so that incubation with EDTA-treated blood acts as a non-specific control for activation, obviating the need for incubation in non-specific antibody.

Surface Plasmon Resonance

Surface plasmon resonance (SPR) is a biosensing technique which measures minute changes in refractive index within a few hundred nanometres of a thin metal film (Charles SA et al, Biotechnology & Human Predisposition to Genetic Disease, Symposia on Molecular & Cellular Biology, Wiley-Liss, 1990, vol 126, pp 219–228). For instance, sensitive measurements of the interaction of proteins with a metal surface can be made in real time.

Silver films, 50 nm thick, were vacuum deposited onto 25 mm square glass microscope slides. The films were inserted into the SPR refractometer, and subjected to a flow (0.4 ml/min) of 1 µM human immunoglobulin G for 10 minutes. The change in resonance angle was monitored continuously, and the total change compared to an untreated film.

EXAMPLE 1

2-[2{2'Pyridyldisulphide}ethoxyhydroxyphosphinyl)-oxy]-N,N,N-trimethylethanaminium hydroxide inner salt

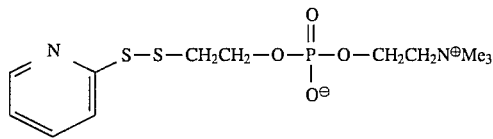

2,2'-Dipyridyl disulphide (15 g, 68 mmol) was dissolved in absolute ethanol (40 ml) and glacial acetic acid (1.4 ml). 2-Mercaptoethanol (3.3 g, 42.5 mmol) in ethanol (20 ml) was added dropwise whilst stirring. The mixture was stirred for 16 hours at ambient temperature when the solvents were removed under vacuum. The residue was treated with benzene and evaporated under reduced pressure three times, and then dried under vacuum. The dried material was chromatographed on silica gel eluting with n-hexane/diethylether mixtures. Fractions containing product were evaporated to give the 2'-pyridyl disulphide -2-ethanol. $^1$H-NMR (CDCl$_3$), 60 MHz, 2.9 (t, 2×H), 3.8 (t, 2×H), 7.0–7.6(m, 3×H), 8.4 (d, 1×H)ppm.

2-'Pyridyldisulphide-2-ethanol (5.3 g, 28 mmole) was stirred in dry acetonitrile (80 ml) together with anhydrous sodium carbonate (200 mg) under nitrogen for 90 minutes. Further 2-chloro-2-oxo-1,3,2-dioxaphospholane (1 g, 7 mmol) was added and stirring maintained for 30 minutes. The mixture was filtered under nitrogen and carefully added to frozen trimethylamine (4.8 ml, 3.15 g, 53 mmol) in a pressure tube which was sealed and heated at 70° C. for 16 hours. The excess trimethylamine was removed, and the solvent evaporated under reduced pressure. The residue was chromotographed on silica gel, eluting with methanol. Fractions containing product were combined, evaporated and the residue triturated successively with acetone and diethylether. Chloroform was added to the residue followed by acetone until a pale gum was deposited. The solvents were decanted, the gum washed with acetone and the residue dried under vacuum for three hours to give 2-[2{2'pyridyldisulphide}ethoxyhydroxyphosphinyl)oxy]-N,N,N-trimethylethanaminium hydroxide inner salt H$^1$-NMR (300MHz) CD$_3$OD: 3.10 (t, 2×H), 3.2 (s, 9×H), 3.60 (m, 2×H), 4.1 (q, 2×H), 4.25 (m,2×H), 7.2 (t, 1×H), 7.6–7.9 (m, 2×H), 8.4 (d,1×H)ppm.

Mass Spectrum, FAB, M$^+$=353.

EXAMPLE 2

2-[(6-Bromohexoxyhydroxyphosphinyl)oxy]-N,N,N-trimethylethanaminium, inner salt

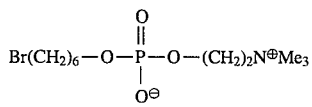

6-Bromohexan-1-ol (1 g, 5.5 mmol), 2-chloro-2-oxo-1,3, 2-dioxaphospholane (0.78 g, 5.5 mmol) and anhydrous sodium carbonate (580 mg) were taken in dry acetonitrile (50 ml) and stirred under nitrogen at ambient temperature for 90 minutes. The mixture was filtered under nitrogen and the filtrate evaporated to a smaller volume (ca 20 ml). The solution was added to frozen trimethylamine (0.5 ml, 5.5 mmol) in a pressure vessel which was sealed and heated at 60° C. for 96 hours. The mixture was filtered and the filtrate partitioned between chloroform (100 ml) and water (100 ml). The aqueous layer was evaporated under reduced pressure and the residue chromatographed on silica gel, eluting with methanol. Fractions containing the compound were combined, evaporated under reduced pressure, treated with benzene and evaporated under reduced pressure and then dried under vacuum to give 2-[(6-bromohexoxy hydroxy phosphinyl)oxy]-N,N,N-trimethylethanaminium, inner salt $^1$H-NMR (300MHz) CD$_3$OD: 1.40–1.60 (m, 4×H), 1.60–1.75 (m, 2×H), 1.75–1.90 (m, 2×H), 3.12 (s, 9×H), 3.3 (m, 2×H), 3.70 (q, 2×H), 3.8–4.1 (m, 4×H)ppm.

EXAMPLE 3

2-[6-Mercaptohexoxyhydroxyphosphinyl)oxy]-N,N,N-trimethylethanaminium, inner salt 2-[(6-Bromohexoxyhydroxyphosphinyl)oxy]-N,N,N-trimethyl ethanaminium, inner salt (100 mg, 0.29 mmol) and a solution of sodium thiosulphate (0.1M, 300 µl) were combined. Methanol (5 ml) was added and the mixture was heated at 80° C. for one hour. Further sodium thiosulphate (0.1M, 3 µl) was added followed by hydrochloric acid (1.0M) until the pH reached 1.0. The mixture was heated at 80° C. for 16 hours. The solvents were evaporated under reduced pressure to leave 2-[6-mercaptohexoxynydroxyphosphinyl)oxy]-N,N,N-trimethylethanaminium, inner salt as a gum containing inorganic salts.

EXAMPLE 4

2[N (3-(2-Pyridyldithio)propionyl) (6-aminohexoxvhydroxy-phosphinyl)oxy-N,N,N-trimethylethanaminium hydroxide, inner salt

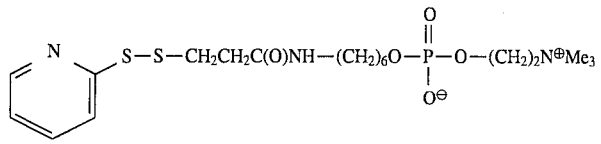

2-[(6-Aminohexoxyhydroxyphosphinyl)oxy-N,N,N-trimethylethanaminium hydroxide, inner salt (90 mg, 0.28 mmol) was dissolved in dry dimethyl sulphoxide (2 ml). Triethylamine (197 µl, 1.41 mmol) was added, followed by N-succinimidyl 3-(2-pyridyldithio)propionate (88 mg, 0.28 mmol). The mixture was stirred at ambient temperature for eighteen hours. The solvent was evaporated under vacuum at a temperature of 60° C. and re-evaporated from methanol. The residue was chromatographed on silica gel eluting with methanol. The relevant fractions were combined and evaporated to dryness to give 2[N(3-(2 pyridyldithio)propionyl)(6-aminohexoxyhydroxy inner phosphinyl)oxy-N,N,N-trimethylethanaminium hydroxide, salt $^1$H-NMR (300MHz) (CD$_3$OD) 1.2–1.9 (m, 8×H), 2.6 (t, 2×H), 3.2 (m, 2×H), 3.26 (s, 9×H), 3.6 (m, 2×H), 3.8 (m, 2×H) , 4.3 m,2×H), 7.2 (t, 1×H), 7.8 (n, 2×H), 8.4 (d, 1×H)ppm.

EXAMPLE 5

A silver coated substrate was washed with ethanol and dried under vacuum. The substrate was placed in a solution of [2{2'-pyridyldithio}ethoxy-hydroxyphosphinyl)oxy]-N,N,N-trimethylethanimium hydroxide, inner salt (164 mg, 0.46 mmol) in ammonium dihydrogen phosphate buffer (pH 7.5, 2 ml). The reaction mixture was left for 24 hours at ambient temperature. The substrate was removed and successively washed with ammonium dihydrogen phosphate buffer (pH 7.5), water and methanol. The substrate was dried under vacuum to give a substrate with a coating of phosphonyl choline derivative.

EXAMPLE 6

(12-MercaptododecoxVhydroxyphosphinyl)oxy-N,N,N,-trimethylethaninium hydroxide, inner salt

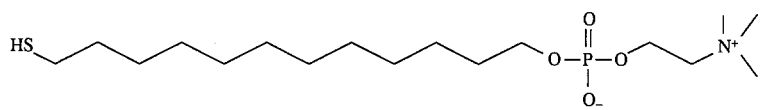

Trityl mercaptan (1.1 g, 4 mmoles) was dissolved in ethanol (60 ml) and water (60 ml) and stirred under nitrogen. Potassium carbonate (0.7 g, 4 mmole) was added and the mixture stirred at ambient temperature for 30 minutes.

12-Bromododecan-1-ol (1 g, 4 mmole) was added and the mixture heated at 80° C. for 16 hours. After cooling, a pink solution separated out, which was decanted. The residue was azeotroped with benzene to give 12-tritylthiododecan-1 -ol (1.53 g, 3.31 mmole, 83% yield).

12-Tritylthiododecan-1-ol (1.53 g, 3.31 mmole) was dissolved in dry acetonitrile (40 ml) and anhydrous sodium carbonate (80 mg) followed by 2-chloro-2-oxo-1,3,2-dioxaphospholane (0.50 g, 3.5 mmole) in acetonitrile (20 ml) were added. The mixture was stirred under nitrogen for two hours. The reaction mixture was filtered, added to an excess of trimethylamine in acetonitrile and heated at 70° C. for 24 hours. After cooling, a yellow liquor was decanted from the mixture, and the residue was chromatographed on silica gel, eluting with chloroform/methanol (1:1). Fractions containing product were combined, evaporated to dryness and azeotroped with benzene to give (12-tritylthiododecoxyhydroxyphosphinyl) oxy-N,N,N,-trimethyl-ethaniminium hydroxide, inner salt (0.51 g, 0.73 mmole, 22% yield).

(12-Tritylthiododecoxyhydroxyphosphinyl) oxy-N,N,N-trimethylethaniminium hydroxide, inner salt (0.45 g 0.72 mmole), was dissolved in methanol (10 ml) and hydrobromic acid in acetic acid (6.2 ml) was added and stirred for ten minutes. Benzene was added and the mixture azeotroped. The residue was triturated with ethyl acetate (×2) and acetone (×2), dissolved in methanol and reprecipitated with acetone. The solid was chromatographed on reverse-phase silica gel eluting with methanol, and fractions containing product were concentrated to give an impure product, 383 mg. Final purification was achieved by a second reverse-phase chromatography column, eluting with methanol: water (9:1), to give (12-mercaptododecoxyhydroxyphosphinyl)oxy-N,N,N,-trimethylethaninium hydroxide, inner salt, 33 mg, 0.086 mmole, 12% yield.

$^1$H-NMR (CD$_3$OD), 200MHz, 1.34 (m, 16×H), 1.69 (m, 4×H), 2.74 (t, 2×H), 3.29 (s, 9×H), 3.71 (m, 2×H), 3.94 (q, 2×H), 4.34 (m, 2×H)

EXAMPLE 7

(2-mercaptoethoxyhydroxyphosphinyl)oxy-N,N,N,-trimethyletaninium hydroxide, inner salt The compound was prepared by a method analogous to that of Example 6, using 2-bromoethanol in place of 12-bromododecan-1-ol.

$^1$H-NMR (CD$_3$OD), 200MH$_z$, 2.90 (t, 3×H), 3.25 (s, 9×H), 3.73 (m, 2×H), 4.06 (q, 2×H), 4.21 (m, 2×H)

EXAMPLE 8

(6-mercaptohexoxyhydroxyphosphinyl)oxy-N,N,N,-trimethylethaninium hydroxide, inner salt The compound was prepared by a method analogous to that of Example 6, using 6-bromohexan-1-ol in place of 12-bromododecan-1-ol.

$^1$H-NMR (CD$_3$OD), 200MH$_z$, 1.39 (m, 4×H), 1.66 (m, 4×H), 2.68 (t, 2×H), 3.22 (s, 9×H), 3.60 (m, 2×H), 3.85 (q, 2×H).

EXAMPLE 9

The compounds of Examples 6, 7 and 8 were coated onto silver metal substrates using the method of Example 5 and were tested using the assays described above, The results were as follows:

| Example | % reduction fibrinogen immunoassay | % reduction activated platelet immunoassay | % reduction IgG surface plasmon resonance |
|---------|-----------------------------------|-------------------------------------------|-------------------------------------------|
| 7 | 33 | 33 | 24 |
| 8 | 65 | 58 | 24 |
| 6 | 80 | 76 | 83 |

We claim:

1. A compound of formula (I)

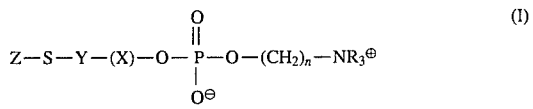

in which the groups R are the same or different and each is hydrogen or a straight or branched $C_1$–$C_4$ alkyl group, n is from 2 to 4, X is a straight or branched $C_{1-30}$ alkylene group, or X is a group of formula —(CH$_2$CH$_2$O)$_b$—, or —(CH$_2$)$_c$—Ar—(CH$_2$)$_d$— where b is from 1 to 20, c and d are the same or different and each is from 0 to 5, and Ar is a para- or meta-disubstituted aryl group, which is optionally further substituted by one or more $C_1$–$C_4$ alkyl groups; and either (a) Y is a valence bond or a divalent functional or heterocyclic group selected from —(X')C(=T)N(H)—, where X' is a straight or branced $C_{1-30}$ alkytene group, or a group of formula —(CH$_2$CH$_2$O)$_b$—, or —(CH$_2$)$_c$—Ar—(CH$_2$)$_d$— where b is from i to 20, c and d are the same or different and each is from 0 to 5, and Ar is a para- or meta-disubstituted aryl group, which is optionally further substituted by one or more $C_1$–$C_4$ alkyl groups and T is oxygen or sulphur, —C(=T)— where T is oxygen, sulphur or NH,
—C(=T)N(H)— where T is oxygen, sulphur or NH, and —Het—Y$^1$— where Y$^1$ is a single bond, oxygen or sulphur, or an alkoxy or alkylthio group containing from 1 to 10 carbon atoms, and Het is a heterocyclic group; and Z is hydrogen or a group —SZ$^1$ where Z$^1$ is an alkyl, cycloalkyl, alkylcycloalkyl, aryl, alkylaryl, heterocyclic, alkylheteroyclic group or a group of formula (II):

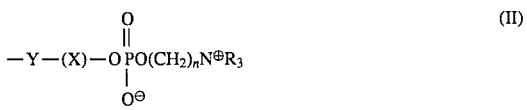

where Y, X, R and n are as hereinbefore defined; or (b) Y is a trivalent alkylene group,
Z is a group —SZ$^1$ and
Z$^1$ is an alkylene group, unsubstituted or substituted by alkyl, aryl, alkylaryl, cycloalkyl or alkylcycloalkyl groups and bonded to the group Y so —Y—S—Z$^1$ form a 5 to 8 membered ring containing a disulphide linkage;

or a hydrate thereof.

2. A compound according to claim 1 in which Z is hydrogen.

3. A compound according to claim 1 in which X is an alkylene group which is a group of formula —(CH$_2$)$_a$—, in which a is from 1 to 30.

4. A compound according to claim 3 in which a is from 12 to 18.

5. A compound according to claim 1 in which Y is a valence bond.

6. A compound according to claim 1 in which each of the groups R is methyl and n is 2.

7. An article having a coated metal surface, which comprises a metal coated on the surface with a compound of formula (I) or a hydrate thereof as claimed in any one of claims 1 to 6.

8. An article according to claim 7 in which the metal surface is a silver or gold surface.

9. A process for useing a compound of formula (I) or a hydrate thereof as claimed in any one of claims 1 to 6, wherein a metal surface is rendered biocompatible, said process comprising applying to the metal surface a coating of a compound of formula (I) or a hydrate thereof as claimed in any one of claims 1 to 6.

10. A process according to claim 9 in which the metal surface is a silver or gold surface.

11. A compound of formula (VI), (VII) or (X)

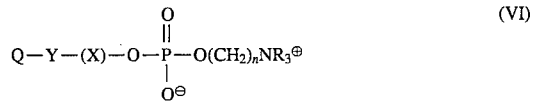
(VI)

where Q is halogen or a protected thiol group, Y is a valence bond or a divalent heterocyclic group and X, R, and n are as defined in claim 1; or

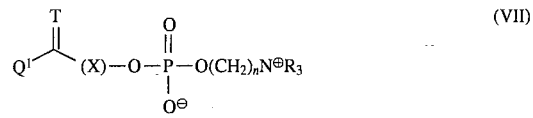
(VII)

where $Q^1$ is halogen or a readily displaceable leaving group, T is oxygen or sulphur, and X, R and n are as defined in claim 1; or

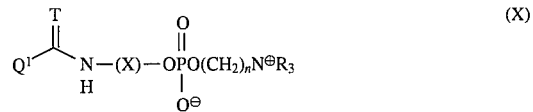
(X)

where $Q^1$ is halogen or a readily displaceable leaving group, T is oxygen or sulphur, and X, R and n are as defined in claim 1.

12. A compound according to claim 11, which is a compound of formula (VI), in which Q is a protected thiol group which is a thioether or thioester group.

* * * * *